US00PP36258P2

(12) United States Plant Patent
Horvath

(10) Patent No.: US PP36,258 P2
(45) Date of Patent: Nov. 19, 2024

(54) ***GERANIUM* MACULATUM PLANT NAMED 'Huggy Bear'**

(50) Latin Name: *Geranium maculatum*
Varietal Denomination: Huggy Bear

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 66 days.

(21) Appl. No.: 18/445,219

(22) Filed: Jun. 5, 2023

(51) Int. Cl.
*A01H 5/02* (2018.01)
*A01H 6/42* (2018.01)

(52) U.S. Cl.
USPC ..... Plt./324
CPC ..... *A01H 6/42* (2018.05)

(58) Field of Classification Search
USPC ..... Plt./324
CPC ..... A01H 5/02
See application file for complete search history.

(56) References Cited

PUBLICATIONS https://www.intrinsicperennialgardens.com/wp-content/uploads/IPG2022_Intros_WEB.pdf; Jan. 2022; 4 pages.*
https://www.instagram.com/p/Cj8_uwqpwOf/; Oct. 20, 2022; 1 page.*

* cited by examiner

*Primary Examiner* — Kent L Bell

(57) ABSTRACT

A new, distinct *Geranium maculatum* plant named 'Huggy Bear' as shown and described, characterized by the combination of chocolate purple 187 A colored new foliage growth and mature foliage and plants that are resistant to foliar diseases.

1 Drawing Sheet

Figure 1:
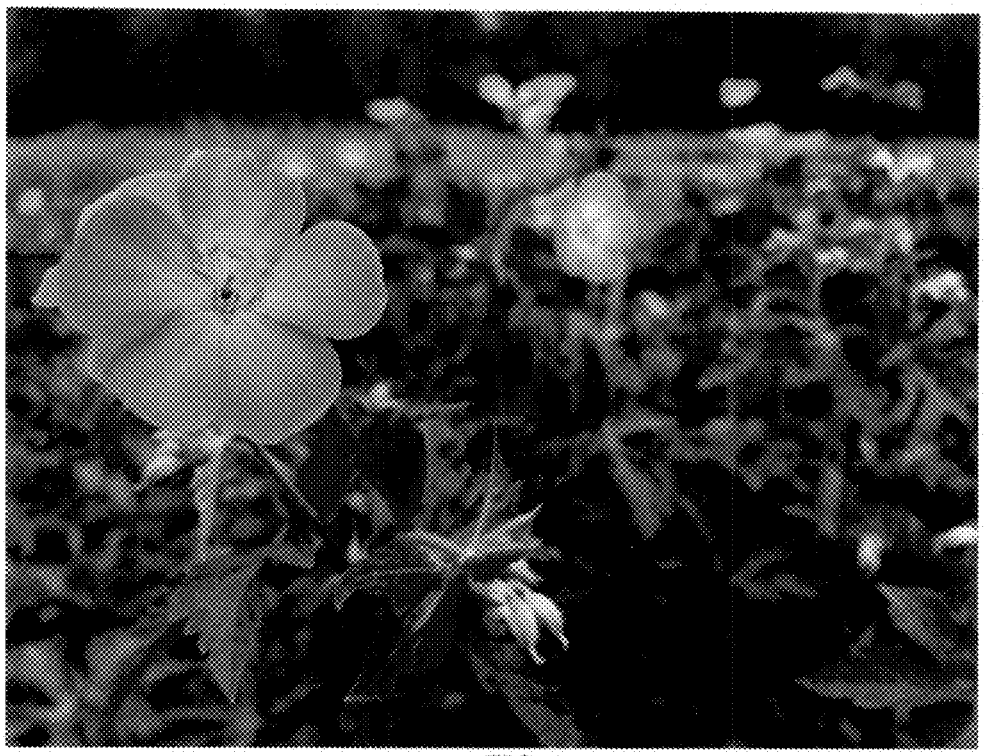

Latin name: *Geranium maculatum.*
Cultivar name: 'Huggy Bear'.

BACKGROUND OF THE INVENTION

The present invention relates to a new and distinct cultivar of *Geranium maculatum* plant, botanically known as *Geranium maculatum* and hereinafter referred to by the name 'Huggy Bear'. The new *Geranium maculatum* 'Huggy Bear' plant is a product of a planned breeding program conducted by the inventor in Hebron, IL, US. The objective of the breeding program is to create vigorous new *Geranium* plants that are resistant to powdery mildew and other common diseases in *Geranium* and was selected for the chocolate purple foliage of its new growth as well as glossy foliage. The new *Geranium maculatum* 'Huggy Bear' plant was discovered and selected by the inventor as a single flowering plant from within the progeny of the stated cross-pollination of a plant of *Geranium maculatum* 'Espresso' (unpatented) as the female parent and an unnamed, unpatented plant of *Geranium maculatum* as the male parent, grown in a controlled environment in Hebron, IL, US during the summer of 2017. Asexual reproduction of the new *Geranium maculatum* 'Huggy Bear' plant by vegetative division in Hebron, IL, US since the summer of 2018, have shown that the unique features of this new *Geranium maculatum* 'Huggy Bear' plant are stable and reproduced true to type in successive generations. No plants of the new *Geranium maculatum* 'Huggy Bear' have been sold in this country, or anywhere in the world, prior to the filing of this application, nor has any disclosure of the new plant been made prior to the filing of this application with the exception of that which was disclosed by the inventor and his nursery, within one year of filing of this application and was derived directly from the inventor. With the first actual sale being on Apr. 4, 2023 in Hebron, IL 60034 US.

SUMMARY OF THE INVENTION

Plants of the *Geranium maculatum* 'Huggy Bear' have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Huggy Bear'. These characteristics in combination distinguish 'Huggy Bear' as a new and distinct *Geranium maculatum* plant:

1. *Geranium maculatum* 'Huggy Bear' exhibits foliage that is dark purple color, RHS 187 A.
2. *Geranium maculatum* 'Huggy Bear' exhibits leaves that are larger than plants of the species known to the inventor.
3. *Geranium maculatum* 'Huggy Bear' exhibits RHS N87 C colored flowers with green-white 157 C at the base of the petals held on sturdy red stems.

*Geranium maculatum* 'Huggy Bear' can also be compared to *Geranium pratense* 'Hocus Pocus' not patented. 'Hocus Pocus' differs from *Geranium maculatum* 'Huggy Bear' in having a more compact mounded plant habit, dark green and purple foliage and in having blue flowers.

*Geranium maculatum* 'Huggy Bear' can also be compared to the female parent *Geranium maculatum* 'Espresso' not patented. 'Espresso' differs from *Geranium maculatum* 'Huggy Bear' in having smaller foliage and in having lighter pink flowers.

DESCRIPTION OF PHOTOGRAPHS

The accompanying colored photographs illustrate the overall appearance of the new *Geranium maculatum* plant showing the colors as true as it is reasonably possible to obtain in colored reproductions of this type. Colors in the photographs may differ slightly from the color values cited in the detailed botanical description which accurately describe the actual colors of the new *Geranium maculatum* 'Huggy Bear' plant.

FIG. 1. The photograph in FIG. 1 is a view of the plant *Geranium maculatum* 'Huggy Bear' in bloom in May on a one-year old plant in Hebron, IL US.

Figure 2:
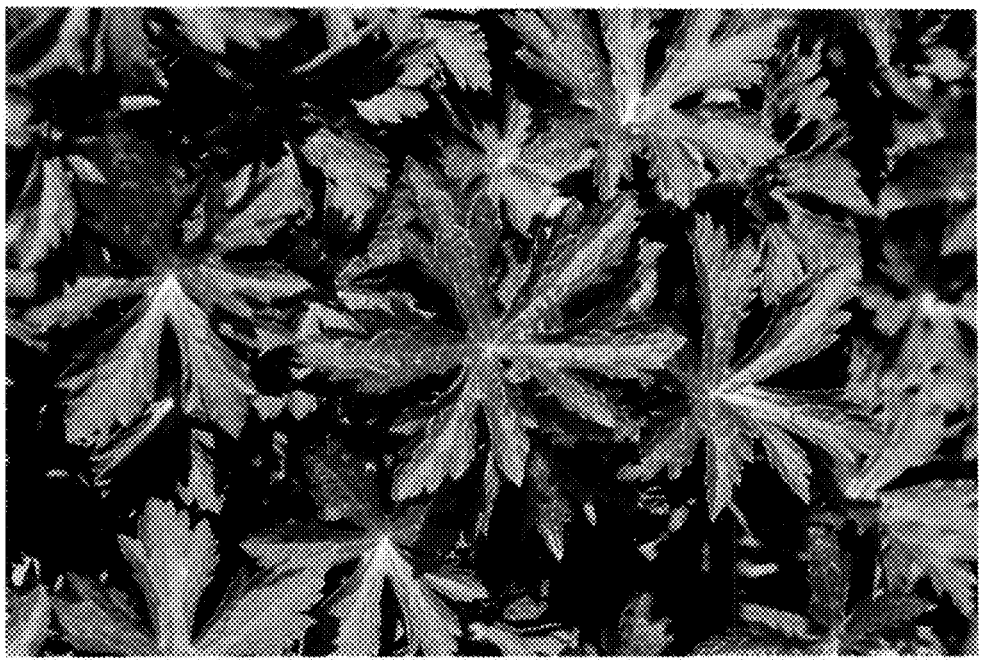

FIG. 2. The photograph in FIG. 2 is a close up of the foliage of *Geranium maculatum* 'Huggy Bear' on a one-year old plant in Hebron, IL US.

The colors of the photographs are as close as possible with the digital photography and printing techniques utilized and the color codes in the detailed botanical description accurately describe the colors of the new *Geranium maculatum* 'Huggy Bear'.

DETAILED BOTANICAL DESCRIPTION

The aforementioned photographs and following observations, measurements and values describe one-year old plants grown during the summer in an outdoor nursery in Hebron, IL US and under typical production conditions. In the detailed description, color references are made to The Royal Horticultural Society Colour Chart, 2001 Edition, except where general terms of ordinary dictionary significance are used.

Plant description:

*Botanical classification.*—*Geranium maculatum* 'Huggy Bear'.

*Blooming period.*—May.

Parentage:

*Female, or seed, parent.*—*Geranium maculatum* 'Espresso'.

*Male, or pollen, parent.*—Unnamed *Geranium maculatum* with deeper pink flowers.

Propagation:

*Type.*—By vegetative division and tissue culture.

*Time to initiate roots, summer.*—About two weeks.

*Time to produce a rooted young plant, summer.*—About two months.

*Root description.*—Fine, fibrous; RHS 177 B in color.

*Rooting habit.*—Fibrous roots extending from stout rootstock.

Plant description:

*Plant and growth habit.*—Herbaceous perennial with broadly upright spreading growth habit. Moderate vigor.

*Plant height.*—30-45 cm. Plant width — 40-50 cm. Aspect: Upright.

Stem description:

*Lateral Branch.*—Typical and observed length — 18 cm, diameter — 2 mm, texture — pubescent, strength — strong, internode length — 12 cm, Stem color — RHS 187 C.

Foliage description:

*Leaf shape.*—Orbicular, palmately cleft with an average of 5-7 lobes.

*Leaf base.*—Semi-peltate. Leaf Apex — Acute.

*Leaf venation.*—Palmate, upper surface 200A in color. Lower surface 182 A and 182 B.

*Leaf margins.*—Palmately cleft, lobes deeply serrate.

*Leaf attachment.*—Petiolate. Leaf Arrangement — Opposite.

*Leaf surface.*—Upper surface: matte, lightly pubescent; Lower surface: sparsely pubescent on main and secondary veins, hairs 0.3 mm in length, approximately 182 A and 182 B in color.

*Leaf color.*—Upper surface: emerging and mature 187 A; lower surface: emerging and mature 177 A.

*Leaf size.*—Average of 6.5 cm in length and 7.5 cm in width.

*Leaf quantity.*—Average of 10 per lateral branch.

*Petioles.*—An average of 9 cm in length and 2 mm in width, color of 187 C, pubescent surface.

*Stipules.*—Two at each leaf base, lanceolate in shape, average of 1 cm in length and 5 mm in width, upper and lower surface 199 D, pubescent on upper and lower surface.

*Durability of foliage to stress.*—High, leaves are thick and sturdy.

Flower description:

*Inflorescence type.*—Umbel.

*Inflorescence size.*—Average of 10-15 cm in height, 10 cm in width.

*Lastingness of flowers.*—About 7 days, self-cleaning.

*Flower size.*—Average of 15 mm in depth and 30 mm in diameter.

*Flower fragrance.*—None.

*Flower number.*—Average of 5 open flowers and 10 buds per lateral branch, about 15 buds and flowers per plant, with 15% open at any stage.

*Flower aspect.*—Outward to slightly upright.

*Flower bud size.*—Average of 7 mm in length, 4 mm in width. Flower Bud color — 138 B.

*Flower bud surface.*—Densely covered with short glandular hairs 1 mm or less.

*Flower bud shape.*—Elliptic.

*Petals typical and observed.*—5, un-fused and arranged in a rotate form, obcordate in shape, entire margins, rounded apex, an average of 15 mm in length and 10 mm in width, color: upper surface opening and fully opened; Top edge of the petal N88 B with the center of the petal N87 C, Veins — both upper and lower surface opening and fully opened; appear color 85 A and 85 B on their edge but are actually clear or translucent; Both upper and lower petal surface: smooth, velvety. Petal base: shape — acute, Texture — glabrous.

*Upper and lower surface color.*—Green-white RHS 157 C but appears as both green and white.

*Calyx.*—Rotate, cupped.

*Sepals.*—Average of 5, ovate to narrowly ovate, entire margins 1 cm, mucronate apex, cuneate base, an average of 9 mm length 4 mm in width, surface dull and glabrous, color: immature and mature upper surface 138 B, mature lower surface 138 B.

*Peduncles typical and observed.*—Round in shape, an average of 13 cm in length and 7 mm in diameter. 146 D in color, held at about a 25 degree angle. Typical and observed Texture — pubescent.

*Pedicel.*—Color 146 D. Length — 5 cm. Width — 3 mm. Typical and observed Texture — pubescent.

Reproductive organs:

*Female.*—Gynoecium — 1 pistil, about 7 mm in length, sitgmas; 5, decurrent, and 138 B in color, style; about 1 mm in length, 145 C in color; ovary; 145 C in color.

*Male*.—Adrocoecium — 10 stamens, anthers; dorsifixed, oblong in shape, 2 mm in length 1 mm in width, and color close to 2 D. Pollen color — 164 B moderate in abundance.

*Fruit*.—Schizocarp, average of 10-12 per lateral branch, 150 per plant, 5 cm in length, 2 mm diameter, 166 A in color. Seed — Average of 5 seeds per fruit, 5 mm in length and 2 mm in diameter; 166 A in color.

Disease resistance: Some resistance to foliar leaf diseases common to *Geranium* has been observed on plants grown under nursery conditions.

Insect resistance: Resistance to insects common to *Geranium* has not been observed on plants grown under nursery conditions.

Hardiness: Plants of the new *Geranium* have been observed to be hardy to USDA Zone 5.

I claim:

1. A new and distinct cultivar of *Geranium maculatum* plant named 'Huggy Bear' as herein illustrated and described.

* * * * *